(12) United States Patent
Geret et al.

(10) Patent No.: US 7,670,549 B2
(45) Date of Patent: *Mar. 2, 2010

(54) MULTIPLE ENZYME CLEANER FOR SURGICAL INSTRUMENTS AND ENDOSCOPES

(75) Inventors: Laurence Geret, Pulheim (DE); Carola Stingl, Düsseldorf (DE); Silke Denzin, Langenfeld (DE)

(73) Assignee: Ecolab Inc., St. Paul, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 12/351,027

(22) Filed: Jan. 9, 2009

(65) Prior Publication Data

US 2009/0192064 A1   Jul. 30, 2009

Related U.S. Application Data

(63) Continuation of application No. 12/020,883, filed on Jan. 28, 2008, now Pat. No. 7,491,362.

(51) Int. Cl.
*A61L 2/16* (2006.01)
*C11D 1/722* (2006.01)
*C11D 3/386* (2006.01)
*B08B 3/04* (2006.01)

(52) U.S. Cl. .................... 422/28; 422/34; 510/161; 510/392; 510/421; 510/475; 510/530; 134/22.19; 134/25.4; 134/39; 134/42

(58) Field of Classification Search ............. 510/161, 510/392, 421, 475, 530; 134/22.19, 25.4, 134/39, 42; 422/28, 34
See application file for complete search history.

(56) References Cited

U.S. PATENT DOCUMENTS

| | | | |
|---|---|---|---|
| 5,066,414 A | 11/1991 | Chang | |
| 5,489,531 A | 2/1996 | Benson | |
| 5,998,342 A | 12/1999 | Scoville, Jr. et al. | |
| 6,100,080 A | 8/2000 | Johansen | |
| 6,204,234 B1 | 3/2001 | Herbots et al. | |
| 6,207,436 B1 | 3/2001 | Bjørnvad et al. | |
| 6,228,128 B1 | 5/2001 | Johansen et al. | |
| 6,251,845 B1 | 6/2001 | Herbots et al. | |
| 6,323,007 B1 | 11/2001 | Moller et al. | |
| 6,380,145 B1 | 4/2002 | Herbots et al. | |
| 6,448,062 B1 | 9/2002 | Huth et al. | |
| 6,555,355 B1 | 4/2003 | Hansen et al. | |
| 6,777,223 B2 | 8/2004 | Xu | |
| 6,797,688 B2 | 9/2004 | Cooper et al. | |
| 6,835,703 B1 * | 12/2004 | Cho et al. | 510/221 |
| 7,056,881 B2 | 6/2006 | Howard et al. | |
| 7,491,362 B1 * | 2/2009 | Geret et al. | 422/28 |
| 2002/0019325 A1 | 2/2002 | Olsen | |
| 2002/0119136 A1 | 8/2002 | Johansen | |
| 2002/0173437 A1 | 11/2002 | Rabon et al. | |
| 2002/0183229 A1 | 12/2002 | Simpson | |
| 2003/0109406 A1 | 6/2003 | Cooney | |
| 2003/0213501 A1 | 11/2003 | Thomson et al. | |
| 2003/0216479 A1 | 11/2003 | Huang et al. | |
| 2003/0220222 A1 | 11/2003 | Kritzler et al. | |
| 2004/0029752 A1 | 2/2004 | Sava et al. | |
| 2006/0030505 A1 | 2/2006 | Biering et al. | |
| 2006/0035800 A1 | 2/2006 | Gibson et al. | |
| 2006/0205626 A1 | 9/2006 | Gant et al. | |
| 2006/0205628 A1 | 9/2006 | Deinhammer et al. | |
| 2006/0270571 A1 | 11/2006 | Burke et al. | |

FOREIGN PATENT DOCUMENTS

| | | |
|---|---|---|
| DE | 102004035881 | 2/2006 |
| FR | 2855973 | 12/2004 |
| WO | WO98/20115 | 5/1998 |
| WO | WO99/11770 | 3/1999 |
| WO | WO2007/007224 | 1/2007 |
| WO | WO2007/057418 | 5/2007 |

* cited by examiner

*Primary Examiner*—Brian P Mruk
(74) *Attorney, Agent, or Firm*—Andrew D. Sorensen; Laura C. Dilorenzo

(57) ABSTRACT

The liquid composition is based on surfactants and enzymes, and is particularly useful for manual cleaning of instruments. In manual and ultrasonic application the composition in use concentration shows low foaming and gives a cleaning solution which is not cloudy at least at a temperature in the range from 16° C. to 40° C. In addition, the composition has good cleaning efficacy over a broad temperature range (20 to 55° C.) and shows good material compatibility.

14 Claims, No Drawings

MULTIPLE ENZYME CLEANER FOR SURGICAL INSTRUMENTS AND ENDOSCOPES

CROSS REFERENCE TO RELATED APPLICATION

This application is a continuation of U.S. patent application Ser. No. 12/020,883, filed Jan. 28, 2008, now issued as U.S. Pat. No. 7,491,362, the entire disclosure of which is incorporated herein by reference in its entirety.

FIELD OF THE INVENTION

The present invention relates generally to compositions and methods for cleaning surgical, medical and dental instruments prior to reuse, and more particularly to treatment of the instruments prior to a disinfection process.

BACKGROUND OF THE INVENTION

Surgical, medical, and dental instruments after use are typically contaminated with blood and other body matter and potentially with infectious microorganisms. Before being reused in a future procedure these instruments must be washed and disinfected where indicated. A typical cycle for cleaning medical instruments consists of a number of consecutive stages: pre-wash, wash, rinses (usually two) and drying. The pre-wash stage is used to dissolve blood on the instruments and may be run with a wash solution containing detergent and possibly enzymes. The wash part of the cycle is run with a wash solution containing detergent and possibly enzymes. Wash time, water temperature and detergent selection and concentration are matched according to requirements. Rinses are used to remove soil dissolved in the wash stage as well as the remaining detergent.

The process of washing and disinfecting becomes complicated when blood or other matter are allowed to dry on the instruments. The body fluids, such as blood, lipids and synovial fluids from joints adhere to the items used during a procedure. As these fluids dry, the adhesion gets stronger and the fluids get harder to dissolve using ordinary cleaning methods. Blood in particular becomes much more difficult to remove once it has dried. Eventually, the adhesion of the soils becomes too strong for normal detergents to break and the instruments remain soiled after cleaning. The chemical structures of these detergents do not allow them to react with body fluids without the body fluids first being changed by other chemicals like enzymes. Enzymes like protease break these body fluids down by the chemical reaction called hydrolysis which also breaks down their adhesive bond to the items the fluids are adhered to. When broken down in this manner, body fluids become more soluble in surfactants and can then be washed away.

The compositions and methods currently used have the drawback that when using them in manual cleaning of instruments the personnel cannot see the items to be cleaned and their contamination when these items are immersed in the wash solution due to the foaming or cloudiness of the solution. It is against this background that the present invention has been made.

DETAILED DESCRIPTION OF THE INVENTION

The object of the present invention was to provide a detergent composition on the basis of surfactants and enzymes, which is particularly useful for manual cleaning of instruments and endoscopes, which shows low foaming in use concentration, which gives a cleaning or wash solution which in use concentration is not cloudy at least at a temperature in the range from 16° C. to 40° C., and further has good cleaning efficacy and material compatibility. This composition is advantageous because it allows personnel to visually monitor the cleaning without foam or cloudy water interfering.

The present invention can be a liquid concentrate composition comprising based on the whole composition a) 1 to 30 wt.-% of a low-foam surfactant system comprising at least two different nonionic surfactants,
   wherein one surfactant (i) is selected from a linear alkoxylated fatty alcohol and an oxo alcohol of the formula $R_1$-A-OH,
   wherein $R_1$ is a linear or branched $C_{10}$ to $C_{16}$ alkyl or alkenyl group,
   wherein A is —$(OC_2H_4)_x$—$(OC_3H_6)_y$— or —$(OC_3H_6)_y$—$(OC_2H_4)_x$—, and
   x is in the range from 7 to 9 (preferably 8), and
   y is in the range from 1 to 3 (preferably 1 to 2), and has a cloud point at a temperature in the range from 64 to 70° C.,
   and the second surfactant (ii) is selected from a linear alkoxylated fatty alcohol and an oxo alcohol of the formula $R_2$-A-OH,
   wherein $R_2$ is a linear or branched $C_{12}$ to $C_{15}$ alkyl or alkenyl group,
   wherein A is —$(OC_2H_4)_x$—$(OC_3H_6)_y$— or —$(OC_3H_6)_y$—$(OC_2H_4)_x$—, and
   x is in the range from 1 to 3 (preferably 2), and
   y is in the range from 4 to 6 (preferably 5), and has a cloud point at a temperature in the range from 39 to 41° C.;
b) at least two different proteases, wherein preferably at least one protease is a serine endopeptidase;
c) lipase;
d) optionally amylase;
e) 10 to 70 wt.-% water and/or a compound of the general formula X—$CH_2$—$(CHY)_n$—$CH_2$-Z (I), wherein n is an integer of from 0 to 2 and X, Y and Z independently symbolize hydrogen or a hydroxyl group provided that at least 2 hydroxyl groups are present; and
f) enzyme stabilizers.

The present invention is particularly useful for manual and ultrasonic cleaning of surgical instruments and endoscopes where visual inspection is helpful. This liquid composition shows low foaming in use concentration and gives a solution which in use concentration is not cloudy at a temperature in the range from 0 to 55° C., preferably from 10 to 50° C. and further preferred from 16° C. to 40° C.

Further, the liquid composition according to the present invention has good cleaning efficacy over a broad temperature range (20 to 55° C.) and shows good material compatibility. In addition the liquid detergent composition according to the present invention also can be used for automated application in washers at a temperature up to about 55° C.

The composition preferably has a pH in the range from 5.5 to 9.0, or in the range from 6.0 to 8.5.

The present invention also provides a use dilution comprising the concentrate according to the present invention diluted with water to a percentage ranging from about 85 to about 0.5 wt.-%.

Surfactant

The composition includes at least two surfactants.

One surfactant (i) is selected from a linear alkoxylated fatty alcohol and an oxo alcohol of the formula $R_1$-A-OH,
wherein $R_1$ is a linear or branched $C_{10}$ to $C_{16}$ alkyl or alkenyl group, wherein A is —$(OC_2H_4)_x$—$(OC_3H_6)_y$— or —$(OC_3H_6)_y$—$(OC_2H_4)_x$—, and x is in the range from 7 to 9 (preferably 8), and y is in the range from 1 to 3 (preferably 1 to 2), and has a cloud point at a temperature in the range from 64 to 70° C., The second surfactant (ii) is selected from a linear alkoxylated fatty alcohol and an oxo alcohol of the formula $R_2$-A-OH, wherein $R_2$ is a linear or branched $C_{12}$ to $C_{15}$ alkyl or alkenyl group, wherein A is —$(OC_2H_4)_x$—$(OC_3H_6)_y$— or —$(OC_3H_6)_y$—$(OC_2H_4)_x$—, and x is in the range from 1 to 3 (preferably 2), and y is in the range from 4 to 6 (preferably 5), and has a cloud point at a temperature in the range from 39 to 41° C.;

The surfactant system provides the detergent solution in use concentration with low-foaming properties and makes it clear or essentially clear at a temperature in the range from 0 to 55° C., preferably in the range from 10 to 50° C. and further preferred in the range from 16 to 40° C. Surfactant (i) has a cloud point at a temperature in the range from 64 to 70° C. and surfactant (ii) has a cloud point at a temperature in the range from 39 to 41° C. The skilled person will understand from the chemical structure of the respective surfactants that the turbidity (cloud point) of the surfactant (i) will be measured in demineralized water while the cloud point of the other surfactant (ii) will be measured in butyl diglycol (5 g of surfactant in 25 ml of 25% aqueous butyl diglycol).

The fatty alcohols appropriate in the present invention can be exemplified by the alcohols obtained from the fatty acids as mentioned above. Oxo alcohols generally represent a mixture of the linear alcohol and the alcohol which is branched with methyl in 2-position. Preferably the alcohol has 10 to 16 and 12 to 15 carbon atoms, respectively. Technical mixtures may additionally contain proportions a different number of carbon atoms.

It is particularly preferred that the sum of nonionic surfactant is present in a concentration ranging from 1 to 20 wt.-%, preferably from 1 to 15 wt.-% and further preferred from 2 to 10 wt.-%

Enzymes

The enzyme system includes at least two different proteases and a lipase and optionally an amylase. The purpose of the enzyme system is to break down adherent proteinaceous materials typically found on instruments after use, into forms that are readily dispersed into a water-based wash solution. Proteins left in or on implements such as instruments that cannot be mechanically scrubbed may prevent chemical disinfecting agents to perform in an efficient way.

Any protease or mixture of proteases, from any source, can be employed in the enzyme system, provided that the selected enzyme system is stable in the desired pH range and compatible with the inventive composition. In a preferred embodiment two different proteases are of the serine endopeptidases type. While the enzyme may be obtained commercially in a solid or liquid form, the liquid form is preferred for greater convenience in dispersing the enzyme during preparation of the concentrated cleaning solution of the invention and for complete water dissolution of the enzyme.

Preferred protease enzymes are stable at least in a pH range of 5 to 8, and are obtained from bacterial strains and have sufficient activity per gram of enzyme protein to economically solubilize and remove proteins from instruments during the desired cleaning cycle.

Suitable protease enzymes are, for example, the enzymes obtained from *Bacillus subtilis*, *Bacillus licheniformis* and *Streptomyces griseus*. More preferably, the enzyme is one or more of the commercially available serine endoproteases. These enzymes preferably cleave protein links on the carboxyl side of hydrophobic amino acid residues, but are capable of cleaving most peptide links. They convert their substrates into small fragments that are readily dissolved or dispersed into a wash solution.

Exemplary proteases are commercially available under the trade name of Everlase® 16 L, Liquanase®, Savinase®, Esperase® (Novozymes) or Purafect® Prime L, Purafect L, Purafect Ox, Prosperase (Genencor) or Blap®. Lipases are commercially available under the trade name Lipex®, or Lipolase® (Novozymes).

Amylases may also be included in the cleaning and detergent composition of the present invention for removing carbohydrate-based foreign materials from medical instruments to be cleaned. Amylase enzymes can be obtained from any suitable source, such as bacterial strains, barley malt, certain animal glandular tissues and any others known to the art. Preferred amylase enzymes are stable in a pH range of 5 to 8, and are obtained from bacterial strains. Preferred types of amylases include those which are referred to as alpha-amylases, beta-amylases, iso-amylases, pullulanases, maltogenic amylases, amyloglucosidases, and glucoamylases, as well as other amylases enzymes not particularly elucidated here. These include also endo- and exo-active amylases. Such amylases are commercially available under the trade name Purastar® ST, Purastar® HP AmL (Genencor), Stainzyme®, Duramyl®, Termamyl®, Termamyl® Ultra (Novozymes).

In a preferred embodiment the composition comprises 0.05 wt.-% to 10.0 wt.-% of at least two different proteases, 0.05 wt.-% to 3.0 wt.-% of lipase and optionally 0.05 wt.-% to 3.0 wt.-% of amylase.

Enzyme Stabilizers

Preferred enzyme stabilizers include boron compounds or a calcium salts. More preferred, the enzyme stabilizers are a boron compound selected from the group consisting of boronic acid, boric acid, borate, polyborate and combinations thereof and wherein the boron compound is present in a concentration ranging from about 0.2% to about 10% by weight. When calcium salts are used the calcium ion concentration is in the range from 0.01 wt.-% to 3.0 wt.-%.

Water and Solvents

The concentrate composition preferably includes water ranging in a concentration of 50 wt.-% or less, preferably of 20 wt.-% or less, further preferred of 15 wt.-% or less. The low amount of water contributes to the stabilization of the enzymes during storage.

In addition to water, the composition may also include a solvent such as an alkanol or a polyol The alkanol is preferably soluble or miscible with water and lipids, and comprises a $C_1$ to $C_{10}$ alkyl group that is straight or branched, substituted or non-substituted. Useful alkanols include short chain alcohols, such as C1-C8 primary, secondary and tertiary alcohols, e.g., methanol, ethanol, n-propanol, iso-propanol, and butanol. Particularly preferred alkanols include the various isomers of C3 alcohols, particularly iso-propanol. C1-C8 diols may also be used in the alkanol constituent. The alkanol is present in a suitable concentration, generally ranging from about 2 to about 10 percent, by weight, relative to the weight of the concentrate. Preferably, the alkanol concentration ranges from about 3 to about 10% by weight, and/or from about 7% to about 10%, by weight, of the enzyme-based aqueous cleaning compositions, i.e., the concentrate according to the invention.

The polyol is preferably an alkylene glycol, such as ethylene glycol or propylene glycol. The polyols represented by the general formula (I) are exemplified by ethylene glycol, 1,2-propylene glycol, 1,3-propylene glycol, glycerine, 1,4-butylene glycol and mixtures thereof, wherein 1,2-propylene glycol is most preferred. The inventive composition contains water and/or the compound of formula (I) in an amount of from 10 to 70 wt.-%, preferably from 30 to 65 wt.-%, wherein the water content preferably is 50 wt.-% or less, more preferred 20 wt.-% or less, further preferred 15 wt.-% or less, and the content of the compound of formula (I) preferably ranges from 20 to 55 wt.-%, more preferred from 20 to 50 wt.-%, based on the whole composition.

Additional Adjuvants

The composition according to the present invention preferably is further comprising a metal corrosion inhibitor which is present in a concentration ranging from about 0.050 to about 1 wt.-%.

The enzymes present in the composition may lead to increased foaming. Therefore, the composition preferably is further comprising an anti-foam component, which further preferred is a silicone-based anti-foam component.

The composition can also include an alkanolamine preferably selected from the group consisting of monoalkanolamine, dialkanolamine, trialkanolamine, alkylalkanolamine, trialkylamine, triethanolamine and combinations thereof, in a concentration ranging from about 1% to about 10 wt.-%. The alkanolamine serves as pH adjustment.

Method of Use

The object of the present invention was also solved by a method for preparing a detergent solution in use concentration which is intended to be used for cleaning or pre-cleaning of surgical, medical or dental instruments or endoscopes by diluting the concentrate according to the present invention as outlined above with water to a percentage ranging from about 85 to about 0.5 wt.-%, wherein the detergent solution in use concentration has low-foaming properties and is clear or is essentially clear at a temperature in the range from 0 to 55° C., preferably in the range from 10 to 50° C. and further preferred in the range from 16 to 40° C.

Further, the present invention provides a method of cleaning or pre-cleaning surgical, medical or dental instruments, or endoscopes by contacting the items with an effective amount of the liquid detergent composition according to the present invention as described above, for a sufficient time to remove substantially all undesirable foreign matter, and then removing the liquid cleaning and detergent composition from said instruments.

The method is carried out either manually or in ultrasonic application or as automated application in washers, preferably at a temperature in the range from 0 to 55° C., further preferred at a temperature in the range from 10 to 50° C. and even further preferred at a temperature in the range from 16 to 40° C.

In a further preferred method the effective amount of the liquid cleaning and detergent composition is from 0.5 wt.-% to 85 wt.-%, preferably from 0.5 wt.-% to 15 wt.-% in water.

According to the present invention the use dilution of the detergent solution has low-foaming properties and is clear or is essentially clear at a temperature in the range from 0 to 55° C., preferably at a temperature in the range from 10 to 50° C. and further preferred at a temperature in the range from 16 to 40° C. The present invention also provides the use of the liquid detergent composition according to the present invention as described above for cleaning surgical, medical or dental instruments or endoscopes.

Applications where enzymatic cleaning is desirable include the cleaning or pre-soaking of items or objects with metal parts or components that must be cleaned to remove organic or biological materials.

In addition to the above-mentioned advantages, the inventive cleaning solution is substantially non-corrosive to metals such as stainless steel, anodized aluminium, aluminium, copper and brass which are often at risk of damages when soaked in previously available cleaning products.

The cleaning solution provided by the invention can be used for any suitable purpose. Preferably, it is employed as a soak cleaner for medical and surgical instruments, dental hand piece, and the like, for both human and veterinary practice. When used as a soak cleaner, it is applied before the instruments are disinfected. It can also be readily used as a concentrate to be added to ultrasonic baths and to automatic washer, for cleaning more elaborate medical equipment.

When employed in automatic washing systems, it is important that the detergent or surfactant component have low foam characteristics to avoid machine malfunction due to excessive foam formation. The inventive cleaning and detergent solution is readily employed at elevated temperatures, as high as about 55° C.

Foreign matter to be cleaned or removed includes, for example, biological substances, e.g., tissue and blood. Foreign matter also includes other materials such as lubricant, diagnostic and therapeutic compositions, materials for pathology testing, medical or veterinary research, and the like, remaining on instruments after these are employed for their intended use. Foreign matter also includes pathogens including bacteria, viruses, and prions.

The term "instrument" is intended to be defined broadly, to include any items, objects, implements or devices for which the gentle removal of organic or biological substances, such as protein, fats, carbohydrates and similar material is desirable. Simply by way of example and without limitation, instruments are implements employed in patient or client contact (human or veterinary) during the practice of surgery, medicine, dentistry, podiatry, pathology for e.g., therapeutic, diagnostic and/or research purposes. Examples include, surgical instruments, e.g., scalpels, probes, clamps, etc., endoscopes, operating room or dental handpieces, ventilation tubes, and the like. Surgical instruments and equipment inevitably pick up amounts of bio-burden on them after being employed in operations on humans or animals. Surgical instruments include for example rigid and flexible scopes, laparoscopic instruments, trays and anything that gets soiled with body fluids which result in them having varying amounts of bio-burden on them after being so used.

Other devices that may be subjected to the inventive cleaning and detergent composition also include miscellaneous other instruments and/or implements employed in cosmetic and beauty applications. These applications include hair cutting, nail care, body art, skin piercing, collection of body fluids, e.g., blood, and blood separation and fractionation equipment, and similar such applications, that are too numerous to mention. The inventive cleaning solutions are also contemplated to be useful for cleaning implements and items employed in the food processing and pharmaceutical industries.

EXAMPLES

Example 1

General Formulation of the Composition of the Present Invention

The tests in respect to foam performance and cleaning efficiacy was carried out using liquid detergent compositions based on the general composition as shown in table 1 (without enzymes), to which different combinations of enzymes have been added as shown in table 2. The examples shown in table 2 are based on the formulation shown in table 1. The percentage given for the enzymes in table refer to g of the actual product per 100 g of liquid base formulation. The final enzyme concentration is indeed lower.

There are several products on the market based on enzymes and surfactant which are displaying different performances with regard to foam formation, turbidity and cleaning performance. A selection of the products on the market has been used as comparative examples for comparison with the composition of the present invention, such as competitor product A (comprising protease, lipase, amylase and anionic surfactant), competitor product B (comprising enzymes and nonionic surfactant), competitor product C (comprising protease, lipase, amylase and anionic surfactant), competitor product D (comprising protease, amylase, lipase, carbohydrase and nonionic surfactant), competitor product E (comprising protease, lipase, amylase and tensides), competitor product F (protease and nonionic surfactant).

TABLE 1

General formulation of the concentrate composition according to the present invention without enzymes.

| component | weight-% |
| --- | --- |
| water | 15.0 |
| glycol | 47.5 |
| corrosion inhibitor | 0.5 |
| preservative | 0.5 |
| alkanol | 5.0 |
| enzyme stabilizers | 2.2 |
| alkanolamine | 2.0 |
| emulsifier | 10.0 |
| glycerol | 4.5 |
| defoamer (silicone based) | 0.05 |
| surfactant i) C10-16 oxyalcohol 8 EO 1-2 PO adduct | 4.5 |
| surfactant ii) C12-15 oxyalcohol 5 PO 2 EO adduct | 3.5 |
| enzymes | ad 100.0 |

TABLE 2

The examples shown in this table are based on the formulation as described in table 1.

| test solution | Protease [wt.-%] | | | | | Lipase [wt.-%] | Amylase [wt.-%] | | | | |
| --- | --- | --- | --- | --- | --- | --- | --- | --- | --- | --- | --- |
| | A | B | C | D | E | A | A | B | C | D | E |
| 23 | — | — | — | — | — | — | — | — | — | — | — |
| 24 | 3 | — | — | — | — | — | — | — | — | — | — |
| 25 | — | 3 | — | — | — | — | — | — | — | — | — |
| 26 | — | — | 3 | — | — | — | — | — | — | — | — |
| 27 | — | — | — | 3 | — | — | — | — | — | — | — |
| 28 | — | — | — | — | 3 | — | — | — | — | — | — |
| 29 | — | 3 | 3 | — | — | — | — | — | — | — | — |
| 30 | — | 3 | — | — | — | 3 | 1.5 | — | — | — | — |
| 31 | — | — | 3 | — | — | 3 | 1 | — | — | — | — |
| 32 | — | 3 | 3 | — | — | 3 | 1 | — | — | — | — |
| 33 | — | 3 | — | — | — | 3 | 2 | — | — | — | — |
| 34 | — | 3 | — | — | — | 3 | 2 | — | — | — | — |
| 35 | — | 3 | 3 | — | — | 3 | — | — | — | — | — |
| 36 | — | 3 | 3 | — | — | 2 | — | — | — | — | — |
| 37 | — | 3 | 3 | — | — | 2 | — | 2 | — | — | — |
| 38 | — | 3 | 3 | — | — | — | — | 2 | — | — | — |
| 39 | — | 2 | 2 | — | — | 2 | — | — | — | — | — |
| 40 | — | 1 | 1 | — | — | 1 | — | — | — | — | — |
| 41 | — | 2 | 2 | — | — | 0.5 | — | — | — | — | — |
| 42 | — | 2 | 2 | — | — | 1.5 | — | — | — | — | — |
| 43 | — | 2 | 2 | — | — | 3 | — | — | — | — | — |
| 44 | — | 2 | 2 | — | — | — | — | — | — | — | — |
| 45 | — | 2 | 2 | — | — | 0.5 | 1 | — | — | — | — |
| 46 | — | 2 | 2 | — | — | 0.5 | — | 1 | — | — | — |
| 47 | — | 2 | 2 | — | — | 0.5 | — | — | 1 | — | — |
| 48 | — | 2 | 2 | — | — | 0.5 | — | — | — | 1 | — |
| 49 | — | 2 | 2 | — | — | 0.5 | — | — | — | — | 1 |
| 50 | — | 2 | 2 | — | — | 0.5 | — | — | — | — | 0.5 |
| 64 | — | 2 | 2 | — | — | 0.5 | — | — | — | — | 0.25 |

Example 2

Testing the Blood Cleaning Efficacy

The products were tested regarding the efficiency of blood cleaning. Before the test the contact time is optimized with blood coupons (preparation see description below). Contact time in our test was set to 10 minutes. The procedure is carried out as follows:

Stainless steel coupons are cleaned and degreased for preparation and then weighed. 0.2 g of reactivated sheep blood is given onto a coupon and spread on the surface so that a 3 mm frame stays clean. The coupons are then drying in a drying cabinet for 1 hour at 37° C. After cooling down to room temperature the coupons are weighed again.

In order to perform the test 400 ml use solution of the detergent composition according to the present invention or of the respective competitor product were added into a beaker. The test coupons were immersed in the detergent composition in a use concentration of 0.6% and left for 10 min without agitation. After the contact time the coupons were removed and immersed in clear water for rinsing. Then the test coupons were dried at ambient temperature over night.

The test was evaluated visually and gravimetrically. The weight of the coupons with dried blood minus the weight of clean coupons is equal to the blood load; the weight of cleaned coupons minus the weight of the clean coupons is equal to the blood load after cleaning, namely the remaining blood load. Using this approach the cleaning efficacy can be calculated. The result in form of the cleaning efficacy is given in percent. The tests were repeated minimum three times.

The experiments were carried out at a temperature in the range of 20 to 23° C. and show that the blood cleaning efficiacy increases when protease is added (test solutions No: 24-28) compared to the test solution having the base formulation without any enzymes (No: 23). The addition of a second (different) protease (test solution No: 29, comprising two different proteases) results in a further increased blood cleaning efficacy. The test solutions having one or two different proteases and in addition lipase and/or lipase and amylase (test solutions No: 30-43 and 45-64) also have increased blood cleaning efficacy compared to test solutions only comprising one protease as enzyme.

Example 3

Testing the Blood Cleaning Efficacy at Different Temperatures

The products were tested regarding the efficiency of blood cleaning at different temperatures, namely at 20-23° C., 40° C. and 55° C. The test method is the same as in example 2. The results are shown in table 3. The test solution 23 represents the base formulation without enzymes as shown in table 1. The test solutions A, B, C, D and F represent competitor products as described above. The solution depicted with the number "64" represents the formulation according to the present invention comprising enzymes as listed in table 2.

TABLE 3

Assaying different test solutions and comparative examples in respect to the Blood Cleaning Efficacy at temperatures of 20-23° C., 40° C. and 55° C. for 10 min, n = 3.

| test solution/ (usage concentration [%]) | relative average cleaning efficacy in %, n = 3 | | | + = invention − = comparative example |
|---|---|---|---|---|
| | 20° C. | 40° C. | 55° C. | |
| 23/(0.6) | 98.7 | 93.3 | 93.8 | − |
| 64/(0.6) | 99.6 | 95.1 | 97.9 | + |
| C/(0.5) | 100.0 | 95.7 | 95.5 | − |
| A/(0.8) | 98.6 | 95.8 | 94.5 | − |
| B/(1.0) | 99.2 | 95.7 | 95.4 | − |
| F/(1.0) | 97.9 | 95.4 | 93.6 | − |
| D/(0.4) | 99.2 | 95.3 | 93.5 | − |

The experiments show that the composition according to the present invention No: 64 has comparable well blood cleaning efficacy and at least at a temperature of 55° C. has improved blood cleaning efficiacy compared to other compositions. Therefore, the compositions according to the present invention have advantageous properties over a wider range compared to the compositions of the state of art.1

Example 4

Testing the Foaming Performance

Description of the test in respect to the foaming performance (shaking method)

The use solution (100 ml) is filled into a 250 ml measuring cylinder. The cylinder is closed with a PE plug and tilted 20 times (to upside down). After time points 0 min, 1 minute and after 5 minutes the foam height in the measuring cylinder is measured with a ruler and documented in "mm". This test is repeated minimum three times.

Before the test the measuring cylinder has to be cleaned and rinsed with ethanol for degreasing; and after that rinse with demineralized water.

Description of the Test in Respect to the Foaming Performance in Intensive Foaming Machine The foaming performance of the products in use solution is measured with mechanical action in dependency of the temperature. The intensive foam machine holds a volume of 40 L. The product is added according to the desired use concentration. After the product has been added the mechanical action is started. The mechanical action simulates the situation in an automated washer. The starting temperature is between 20° and 22° C. After the mechanical action has been running for 1 minute the machine is stopped and the foam height documented. Then the agitation is started again and the heating is switched on. In intervals of 2° C. the machine is stopped and the foam height documented. The temperature is raised up to 55° C. to simulate a washer. The foam height is documented in mm. The results are summarized in table 4.

TABLE 4

Foam performance of test solution and comparative examples.

| test solution | foam performance (cm) | | |
|---|---|---|---|
| | 0 min | 1 min | 5 min |
| competitor product A (0.8%) | 7 | 6 | 5 |
| competitor product B (1.0%) | 7.5 | 3 | 0.5 |
| competitor product C (0.5%) | 3 | 1 | 1 |
| competitor product D (0.425%) | 7 | 5 | 4 |
| competitor product E (1.0%) | 15 | 13 | 9 |
| competitor product F (1.0%) | 6.5 | 2 | 1 |
| 64 (invention) | 6 | 2.5 | 1.5 |

The experiments show that the composition according to the present invention No: 64 has low-foaming properties compared to most of other compositions. Therefore the composition of the present invention is particularly useful for manual cleaning of surgical instruments and endoscopes.

In respect to testing the foaming performance in intensive foaming machine method the results show ideal properties of the composition according to the present invention. The foam height was at a temperature from about 20° C. to 42° C. was between 300 to 400 mm, while at a temperature of 44° C., 46° C., 48° C., 50° C. and 52° C. the foam height went down and was 250, 210, 190, 120 and 100 mm, respectively, while at a temperature of 54° C. the foam height was less 20 mm or less.

Example 4

Description of the Assay of the Cloud Point of Products and Use Concentrations

The method is used for the determination of the cloud point in liquid products. The temperature describes the temperature range in which the nonionic surfactant in diluted concentration becomes harder soluble and by that low foaming.

The cloud point is understood as a temperature where the liquid product gets cloudy. The procedure is carried out as follows:

The use concentration is filled into a 150 ml beaker. The temperature is raised slowly and monitored with a thermometer. The temperature at which the product solution shows the first cloudiness during heating is documented. The solution as well as the temperature are observed during cooling and the temperature is documented where the solution first becomes clear again. The cloud point is determined with an accuracy of 0.5° C. The results are summarized in table 5.

TABLE 5

The table summarizes the results of the measurements of the cloud points/turbidity of diverse competitor products and the composition according to the present invention.

| test solution | cloud point in demineralized water |
|---|---|
| competitor product A (0.8%) | n.d. |
| competitor product B (1.0%) | 35° C. |
| competitor product C (0.5%) | n.d. |
| competitor product D (0.43%) | 40.5° C. |
| competitor product E (1.0%) | n.d. |
| competitor product F (1.0%) | 26° C. |
| invention | >55° C. |

The results show that the liquid detergent composition of the present invention gives a cleaning solution which is not cloudy up to a temperature of 55° C. Due to these characteristics the composition of the present invention is particularly useful for manual and ultrasonic application when cleaning surgical instruments and endoscopes.

What is claimed is:

1. A liquid detergent concentrate composition comprising:
  a) 1 to 30 wt.-% of a surfactant system comprising at least two different nonionic surfactants, wherein the first surfactant is selected from the group consisting of a linear alkoxylated fatty alcohol and an oxo alcohol of the formula $R_1$-A-OH, wherein $R_1$ is a linear or branched $C_{10}$ to $C_{16}$ alkyl or alkenyl group, wherein A is $-(OC_2H_4)_x-(OC_3H_6)_y-$ or $-(OC_3H_6)_y-(OC_2H_4)_x-$, and x is from 7 to 9, and y is from 1 to 3, and the first surfactant has a cloud point at a temperature in the range from 64 to 70° C., and the second surfactant is selected from the group consisting of a linear alkoxylated fatty alcohol and an oxo alcohol of the formula $R_2$-A-OH, wherein $R_2$ is a linear or branched $C_{12}$ to $C_{15}$ alkyl or alkenyl group, wherein A is $-(OC_2H_4)_x-(OC_3H_6)_y-$ or $-(OC_3H_6)_y-(OC_2H_4)_x-$, and x is from 1 to 3, and y is from 4-6, and the second surfactant has a cloud point at a temperature in the range from 39 to 41° C.;
  b) at least two different proteases;
  c) 10 to 70 wt.-% water; and
  d) an enzyme stabilizer.

2. The composition of claim 1, wherein the sum of nonionic surfactant is present in a concentration ranging from 1 to 20 wt.-%.

3. The composition of claim 1, wherein when the concentrate is diluted to form a use composition the use composition is low-foaming and essentially clear at a temperature in the range from 0 to 55° C.

4. The composition of claim 1, wherein each of the different at least two proteases is a serine endopeptidase.

5. The composition of claim 1, wherein the water is present in a concentration of 50 wt.-% or less.

6. The composition of claim 1, wherein the enzyme stabilizer is selected from the group consisting of a boron compound and a calcium salt.

7. The composition of claim 1, wherein the enzyme stabilizer is a boron compound selected from the group consisting of boronic acid, boric acid, borate, polyborate and combinations thereof and wherein the boron compound is present in a concentration ranging from about 0.2% to about 10% by weight.

8. The composition of claim 1, further comprising an alkanolamine selected from the group consisting of monoalkanolamine, dialkanolamine, trialkanolamine, alkylalkanolamine, trialkylamine, triethanolamine and combinations thereof, in a concentration ranging from about 1% to about 10 wt.-%.

9. The composition of claim 1, wherein the composition further comprises at least one alkanol, wherein the alkanol is soluble or miscible with water and lipids, and comprises a $C_1$ to $C_{10}$ alkyl group that is straight or branched, substituted or non-substituted.

10. The composition of claim 1, further comprising a metal corrosion inhibitor present in a concentration ranging from about 0.050 to about 1 wt.-%.

11. The composition of claim 1, further comprising a silicone-based anti-foam component.

12. The composition of claim 1, having a pH in the range from 5.5 to 9.0.

13. The composition of claim 1, further comprising an additional enzyme selected from the group consisting of lipase, amylase and mixtures thereof.

14. A method of cleaning instruments or endoscopes comprising:
  (a) contacting the instrument or endoscope with an effective amount of the liquid detergent composition comprising
    1 to 30 wt.-% of a low-foam surfactant system comprising at least two different nonionic surfactants, wherein the first surfactant is selected from the group consisting of a linear alkoxylated fatty alcohol and an oxo alcohol of the formula $R_1$-A-OH, wherein $R_1$ is a linear or branched $C_{10}$ to $C_{16}$ alkyl or alkenyl group, wherein A is $-(OC_2H_4)_x-(OC_3H_6)_y-$ or $-(OC_3H_6)_y-(OC_2H_4)_x-$, and x is from 7 to 9, and y is from 1 to 3, and the first surfactant has a cloud point at a temperature in the range from 64 to 70° C., and the second surfactant is selected from the group consisting of a linear alkoxylated fatty alcohol and an oxo alcohol of the formula $R_2$-A-OH, wherein $R_2$ is a linear or branched $C_{12}$ to $C_{15}$ alkyl or alkenyl group, wherein A is $-(OC_2H_4)_x-(OC_3H_6)_y-$ or $-(OC_3H_6)_y-(OC_2H_4)_x-$, and x is from 1 to 3, and y is from 4-6, and the second surfactant has a cloud point at a temperature in the range from 39 to 41° C.;
    at least two different proteases;
    10 to 70 wt.-% water; and
    enzyme stabilizers; and
  (b) removing substantially all undesirable foreign matter from the instrument or endoscope; and
  (c) rinsing the instruments or endoscope.

* * * * *